(12) United States Patent
Leopoldo da Camara Filho

(10) Patent No.: US 10,953,266 B2
(45) Date of Patent: Mar. 23, 2021

(54) SYSTEM FOR PERFORMING PHYSICAL EXERCISES AT A CONSTANT SPEED OF A MOVEMENT

(71) Applicant: Carlos Alberto Leopoldo da Camara Filho, Rio de Janeiro RJ (BR)

(72) Inventor: Carlos Alberto Leopoldo da Camara Filho, Rio de Janeiro RJ (BR)

(*) Notice: Subject to any disclaimer, the term of this patent is extended or adjusted under 35 U.S.C. 154(b) by 0 days.

(21) Appl. No.: 16/309,553

(22) PCT Filed: Jan. 24, 2017

(86) PCT No.: PCT/BR2017/000005
§ 371 (c)(1),
(2) Date: Dec. 13, 2018

(87) PCT Pub. No.: WO2017/219103
PCT Pub. Date: Dec. 28, 2017

(65) Prior Publication Data
US 2019/0160324 A1   May 30, 2019

(30) Foreign Application Priority Data
Jun. 21, 2016 (BR) .................... 102016014608-9

(51) Int. Cl.
*A63B 21/00* (2006.01)
*A63B 24/00* (2006.01)
(Continued)

(52) U.S. Cl.
CPC .............. *A63B 21/152* (2013.01); *A61B 5/22* (2013.01); *A63B 21/00* (2013.01); *A63B 21/022* (2015.10);
(Continued)

(58) Field of Classification Search
CPC ......... A63B 21/52; A63B 24/00; A63B 21/00; A63B 21/022; A63B 2071/0683;
(Continued)

(56) References Cited

U.S. PATENT DOCUMENTS

| 4,772,015 A | 9/1988 | Carlson et al. |
| 4,778,175 A | 10/1988 | Wucherpfennig et al. |

(Continued)

FOREIGN PATENT DOCUMENTS

| BR | 102012011320 A2 | 4/2014 |
| CN | 203539973 U | 4/2014 |

(Continued)

OTHER PUBLICATIONS

International Search Report for PCT/BR2017/000005, dated Jun. 26, 2017.

(Continued)

*Primary Examiner* — Andrew S Lo
(74) *Attorney, Agent, or Firm* — Bacon & Thomas, PLLC

(57) ABSTRACT

The present invention applies to the field of exercise devices and bodybuilding and muscle building devices. This invention describes a system applied in exercise devices, preferably for the performance of the activity of bodybuilding, without the use of a counterweight, in which the system is based on the speed of the movement, independent of the applied force.

11 Claims, 3 Drawing Sheets

(51) Int. Cl.
  *A63B 21/02* (2006.01)
  *G01L 1/00* (2006.01)
  *A61B 5/22* (2006.01)
  *G05B 19/048* (2006.01)
  *B66D 1/48* (2006.01)
  *G06F 3/041* (2006.01)

(52) U.S. Cl.
  CPC .............. *A63B 24/00* (2013.01); *B66D 1/485* (2013.01); *G01L 1/00* (2013.01); *G05B 19/048* (2013.01); *G06F 3/0416* (2013.01)

(58) Field of Classification Search
  CPC ............ A63B 71/0619; A63B 21/4043; A63B 21/4035; A63B 21/154; A63B 21/153; A63B 21/023; A63B 21/025; A63B 21/015; A63B 21/0058; A63B 21/005; A63B 21/002; A63B 21/00076; A63B 21/00058; A63B 24/0087; A63B 2220/833; A63B 2220/51; A63B 2220/34; A63B 21/008; A63B 2220/30; A63B 21/012–0557; A63B 21/15–156; A63B 22/00–0005; A63B 22/0076–0089; A63B 2022/0079–0084; A63B 23/00; A63B 23/035–04; A63B 23/0087; G05B 19/048; A61B 5/22; G01L 1/00; G06F 3/0416; B66D 1/485
  See application file for complete search history.

(56) References Cited

U.S. PATENT DOCUMENTS

| | | | | |
|---|---|---|---|---|
| 4,919,418 A * | 4/1990 | Miller | A63B 21/151 | 482/112 |
| 5,180,348 A * | 1/1993 | Saarinen | A63B 21/0051 | 482/6 |
| 5,271,416 A * | 12/1993 | Lepley | A63B 21/005 | 600/595 |
| 5,318,491 A * | 6/1994 | Houston | A63B 22/001 | 273/451 |
| 5,328,429 A * | 7/1994 | Potash | A63B 21/0058 | 482/4 |
| 5,435,798 A * | 7/1995 | Habing | A63B 21/00181 | 482/5 |
| 5,697,869 A * | 12/1997 | Ehrenfried | A63B 21/0058 | 482/129 |
| 5,762,584 A * | 6/1998 | Daniels | A63B 21/0056 | 482/5 |
| 6,027,429 A * | 2/2000 | Daniels | A63B 21/0056 | 482/111 |
| 6,280,361 B1 | 8/2001 | Harvey et al. | | |
| 8,845,499 B1 * | 9/2014 | Boatwright | A63B 21/154 | 482/116 |
| 10,143,880 B1 * | 12/2018 | Boatwright | A63B 21/075 | |
| 2007/0240940 A1 * | 10/2007 | Moriarty | A62B 1/12 | 182/238 |
| 2010/0069202 A1 * | 3/2010 | Olsen | A63B 21/0058 | 482/5 |
| 2010/0298104 A1 * | 11/2010 | Turner | A63B 21/00069 | 482/93 |
| 2011/0172058 A1 * | 7/2011 | Deaconu | A63B 22/0012 | 482/5 |
| 2014/0287876 A1 * | 9/2014 | Etter | A63B 24/0087 | 482/5 |
| 2015/0165272 A1 * | 6/2015 | Bird | A63B 24/0087 | 482/5 |
| 2015/0258361 A1 * | 9/2015 | Xie | A63B 21/153 | 482/98 |
| 2016/0114211 A1 * | 4/2016 | Schmidt | A63B 21/002 | 482/5 |
| 2016/0121156 A1 * | 5/2016 | Bach | A63B 21/0087 | 482/112 |
| 2016/0339287 A1 * | 11/2016 | Olson | A63B 24/0062 | |
| 2017/0304680 A1 * | 10/2017 | Schmidt | A63B 21/002 | |
| 2017/0319941 A1 * | 11/2017 | Smith | A63B 71/0686 | |
| 2018/0214729 A1 * | 8/2018 | Rubin | A63B 21/156 | |
| 2018/0214730 A1 * | 8/2018 | Larose | A63B 21/157 | |
| 2018/0318646 A1 * | 11/2018 | Lagree | A63B 24/0075 | |
| 2018/0339196 A1 * | 11/2018 | Richter | A63B 22/0087 | |
| 2018/0353813 A9 * | 12/2018 | Bird | A63B 21/151 | |
| 2019/0105526 A1 * | 4/2019 | Boatwright | A63B 21/4043 | |
| 2019/0126087 A1 * | 5/2019 | Schmidt | A63B 21/157 | |
| 2019/0151716 A1 * | 5/2019 | Bird | A63B 21/0058 | |
| 2019/0262663 A1 * | 8/2019 | Schmidt | A63B 24/0087 | |
| 2019/0269958 A1 * | 9/2019 | Dalebout | A63B 21/0051 | |

FOREIGN PATENT DOCUMENTS

| | | |
|---|---|---|
| CN | 104138652 A | 11/2014 |
| DE | 102011121259 B3 | 5/2013 |

OTHER PUBLICATIONS

Written Opinion for PCT/BR2017/000005, dated Jun. 26, 2017.
International Preliminary Examination Report for PCT/BR2017/000005, dated Jul. 26, 2018.

\* cited by examiner

SYSTEM FOR PERFORMING PHYSICAL EXERCISES AT A CONSTANT SPEED OF A MOVEMENT

This invention applies to the field of exercise devices and bodybuilding and muscle building devices.

The present invention describes a system applied in exercise devices, preferably for the performance of the activity of bodybuilding, without the use of a counterweight, in which the system is based on the speed of the movement, independent of the applied force.

BACKGROUND OF THE INVENTION

The history of bodybuilding is very old. There are historical reports that date back to the beginning of time that confirm the practice of exercising with weights. Excavations have found stones with notches for the hands, allowing historians to deduce that people trained with weights. Sculptures have been found dating back to 400 B.C., which display harmonious shapes of women, indicating a concern with esthetics at the time. There are reports of stone throwing games, dating back to 1896 B.C., as well as the walls of tombs in Egypt, which display men lifting weights for exercise 4,500 years ago.

From the end of the nineteenth century, history shows that "bodybuilding" along with "weightlifting" became attractions at the circus and theaters, where "the strongest men in the world" were on show. Historically, bodybuilding is presented as one of the oldest physical activities in the world, because there are historical accounts dating from the beginning of time to confirm exercising with weights.

Bodybuilding as a form of competition, where the muscles are displayed, had its first official competition in London, in 1901.

Bodybuilding or strength training is well-known and is a method of resistance exercise, aimed at the training and the development of the skeletal muscles. It is known in the state of the art that this type of exercise uses the force of gravity (with counterweights such as bars, dumbbells, weights or the weight of the body) and the resistance generated by devices, elastic and springs to oppose forces to the muscles, which, in turn, generate an opposite force by the muscle contractions that may be concentric, eccentric or isometric.

The Brazilian document BR 10 2012 011320 1 describes a system for bodybuilding devices, in which the initial movement of the equipment is performed without any effort by the user and, when reaching the determined position of its path, the system begins to exert the force automatically in the opposite direction. The first part of the movement described in this document, which is the concentric movement, is performed without any load, and aims only to position the bar/pedal for the start of the exercise, which is done eccentrically, with counterweights previously selected by the user. The document does not describe how the weights are conveyed into this condition for a subsequent return to the rest position, where the user performs the eccentric force movement, which differs from the present invention.

The Chinese document CN 104138652A describes a device using a magnetic force, which acts as a source of counterweight. This document differs from the present invention because the mechanism used (magnetic force) acts as a counterweight and the resistance is predetermined.

The Chinese document CN 203539973 U describes counterweight blocks for bodybuilding equipment. This differs from the present invention, which does not use a counterweight for the performance of the exercise.

SUMMARY OF THE INVENTION

The present invention describes a system for the performance of exercise without the use of counterweights.

The said system is based on the speed of the movement, independent of the applied force, thereby breaking with the conventional relation between speed and force.

The system described herein represents a paradigm shift in relation to the conventional systems described in the state of the art, whose weight load (and therefore the employed force) is previously regulated in the system.

BRIEF DESCRIPTION OF THE FIGURES

The invention can be better understood through the brief description of the following figures.

DETAILED DESCRIPTION OF THE INVENTION

Figure 1:
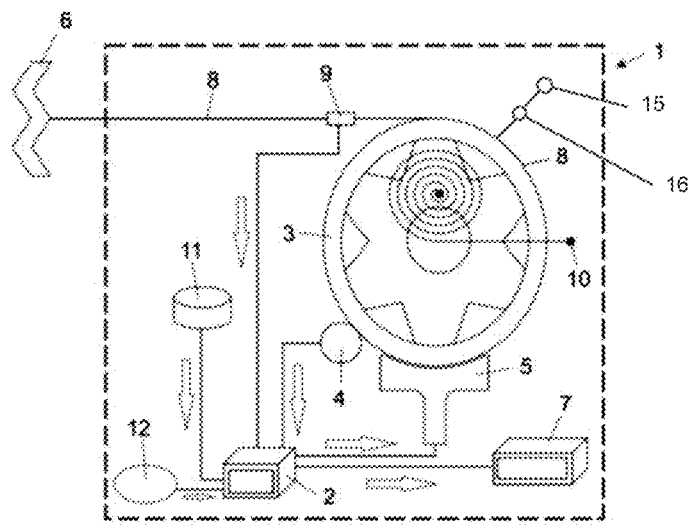
FIG. 1 represents the operation of the system for the performance of the exercise without the use of counterweights.

The present invention describes a system (1) for the performance of exercise without the use of counterweights. The system (1) for the performance of exercise without the use of counterweights comprises a microprocessor (2), which determines the operation of the brake (5) based on speed that is predetermined by the user and the instantaneous speed that is being measured by the speed sensor (4), and also, which receives information from the speed sensor (4), from the dynamometer (9) and from the speed selector (11), which operates with a pulley (3). This operation occurs when the speed, after being regulated by the speed selector (11), which can be, for example, a keyboard, an analog potentiometer, + and—buttons, i.e., any type of selector that specifies the intended speed, is being constantly measured by the speed sensor (4), which forwards the information to the microprocessor (2). This, in turn, controls the brake (5) of the pulley (3 or 3'), seeking to maintain the constant rotation speed, previously specified by the speed selector (11), as well as a steel cable (8), containing an installed dynamometer (9), a load sensor, which supplies information regarding the applied force, which is translated and displayed on the digital panel (7). The steel cable (8) is attached to the pulley (3) and connected to the support bar (6), which translates the employed force displayed on the digital panel (7), where a minimum force is required to overcome the resistance of the spring (10).

The system for the performance of exercise without the use of counterweights is controlled by a microprocessor (2), which receives information from the sensors and determines the adjustments required to limit the speed of the movement in accordance with the adjustment made by the user, operating with a pulley (3), which is 20 to 60 cm in diameter and has 90 cm to 250 cm of cable. These measures may vary depending on the type of device.

The operation of the pulley (3) occurs when the speed, after being regulated by the user (11), is constantly measured by a sensor (4). There are several types of speed sensors (4), both analog and digital. An example of a sensor that can be used in the present invention is the optical sensor, which is capable of informing the RPM to the microprocessor. In order to facilitate the use in the present invention, the user could have 10 adjustment possibilities, for example, from a very slow movement to a very fast movement.

This sensor (4) forwards the information to the microprocessor (2), which, in turn, controls the brake (5) of the pulley (3 or 3'), in order to keep the rotation speed constant.

Once the speed of the movement is regulated in the system (1), this is maintained, whatever the force employed by the person performing the exercise. The force limit is related to the capacity of the brake (5). In the present invention, the force is limited, preferably, up to 300 kg, which is more than in the already known equipment. Preferably, the force should be limited up to 400 kg and, more preferably, up to 500 kg, through the dimensioning of the brake (5), such as, for example, placing more electromagnets and/or more braking elements in order to allow a perfect control of the speed. Therefore, the force applied—whether by a child or by a weightlifter—does not alter the speed of movement of the support bar of the system.

The support bar (6) of the system (1) can be directed to exercise any part of the body, preferably the arms or legs. However, it is not limited to these and the system can be used in different exercises.

The force employed on the bar (6) of the system (1) of the present invention is translated into kilograms, pounds or any other measure of weight that is available in the International System of Units (SI). This is continuously displayed on a digital panel (7), preferably composed of an LCD screen. It can also be a digital touch screen panel, or analog or similar. It contains information, such as, for example, the speed and weight adjustments, supplied by the microprocessor, so that the user can regulate, at will, the force employed and, therefore, the weight load of his exercise.

The present invention allows for the load to be programmed and even to be altered by the user, during the exercise, at will. This is because, as the system does not use weights/counterweights, it only uses the control of the speed of the movement of the user, where the force employed in the exercise depends only on the will/capability of the individual.

Therefore, the user is the person who decides the quantity of force to be employed in the exercise.

Furthermore, the user can observe the information of the equivalent amount of kilos "lifted" that is displayed on the digital panel (7). This is increased and reduced by the simple determination of the force being employed on the bar (6), which is measured by the dynamometer (9). Therefore, the "load" is related only to the physical condition of the user, who is entirely capable of increasing or decreasing the force, at will.

Therefore, whereas in the conventional systems the user previously regulated the weight and determined the speed of the exercise during its performance, in the present invention the user previously establishes the speed and employs/alters the force at will.

The brake (5) described here may be a disc, electromagnetic, drum or electro-hydraulic brake, although it is not limited to these. An example of an embodiment of the present invention is the use of the electromagnetic brake, where there is a disk attached to the pulley and two close electromagnets that, when activated, brake the system (Foucault effect). The brake (5), such as, for example, the electromagnetic brake, has a load that varies in accordance with the intensity of the electric voltage. Another example of the operation of the system is the action of a disc brake actioned by a stepper motor, which can be a drum brake or similar.

The entire system described here is controlled by a microprocessor (2), which functions as an interface.

The microprocessor (2), after receiving the information relating to the speed, controls the use of the brake (5), in order to maintain the constant speed predetermined by the user.

The microprocessor (2) described here is equivalent to a computer, only that it is very small and is dedicated solely to this task. The microprocessor (2) receives the information from the speed sensor (4), processes the information (based on the determination of the speed made by the user) and determines the action of the components of the system.

The microprocessor (2) is also entirely capable of controlling the stepper motor with minimal movements, which guarantees high precision in the control of the speed of the movement, in the situation of the brakes being operated by the same.

The system described herein is composed of a computer program—software—(12), which, on the basis of the information received from the sensors (4 and 9) and from the speed selector (11), determines the operation of the brake (5), which can act releasing the pulley (3) (rotating below that programmed) or the contrary.

Only minimal force is required to overcome the resistance of the spring (10) used to bring the system to the initial condition, which is considered negligible. The maximum force is directly related to the brake capacity (5) of the system. It can be built for a maximum load of up to 500 kg, as previously described, depending only on the brake (5).

It is important to observe that in a preferred embodiment of the invention, using a disk brake, driven by a stepper motor, the capacity of the system is much greater.

Furthermore, a steel cable (8) attached to the pulley (3) connects with the support bar (6), which is used for the exercise. The steel cable (8) is 3 to 10 mm thick. However, the diameter varies in accordance with the capacity of the system described herein. In the situation of the force to be employed being 500 kg, the cable must have a larger diameter.

A dynamometer (9), also known as a load sensor, installed on the steel cable supplies the information about the applied force, which is translated preferably in kilograms, and is displayed on the digital panel (7). The dynamometer (9) is required to guarantee the safety of the system. If there is no force being employed, the system interprets that there is no exercise being practiced and interrupts the operation of the motor and returns everything back to the original position.

At the end of the exercise, the pulley (3) returns to the original position, due to the spring (10).

The spring (10) only acts to return the system to the initial position. It is sized to perform only this task, in order to interfere as little as possible during the exercise. One example of a type of spring (10) in the present invention is a spiral spring, taking into account that the pulley can give more than one complete turn. Examples of springs used are, in addition to the spiral spring, a helical or spiral spring, common springs or springs used in conjunction with an electric motor. The size of the spring (10) is proportional to the size of the pulley (3) and it is placed on the opposite side to the brake (5). The spring (10) is attached immediately above the central axis of the pulley (3). The spring (10) has the function of making the system return to the initial position, so that it can be used again.

Because this is a system that uses a microprocessor (2), integration of the said system is foreseen with other digital systems, such as, for example, computers, tablets and smartphones, etc.

Figure 2:
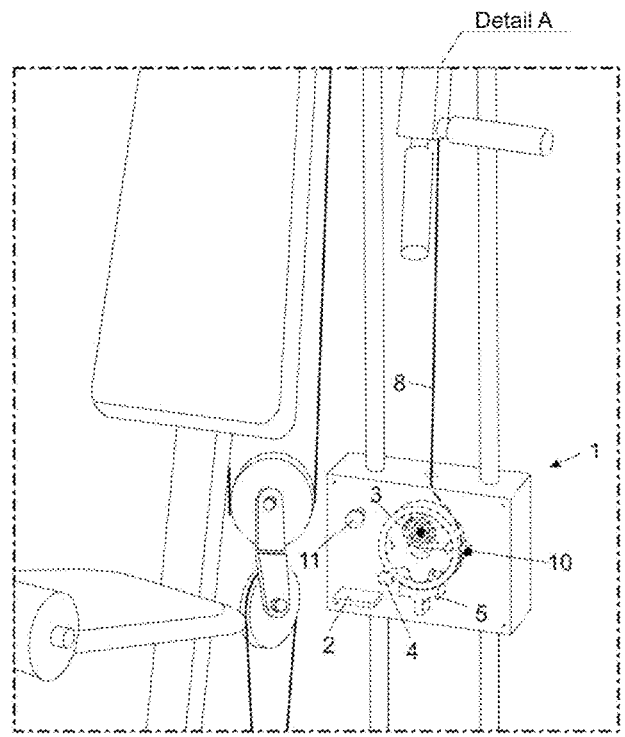
FIG. 2—detail A—represents the system inserted into already known exercise devices.
Figure 3:
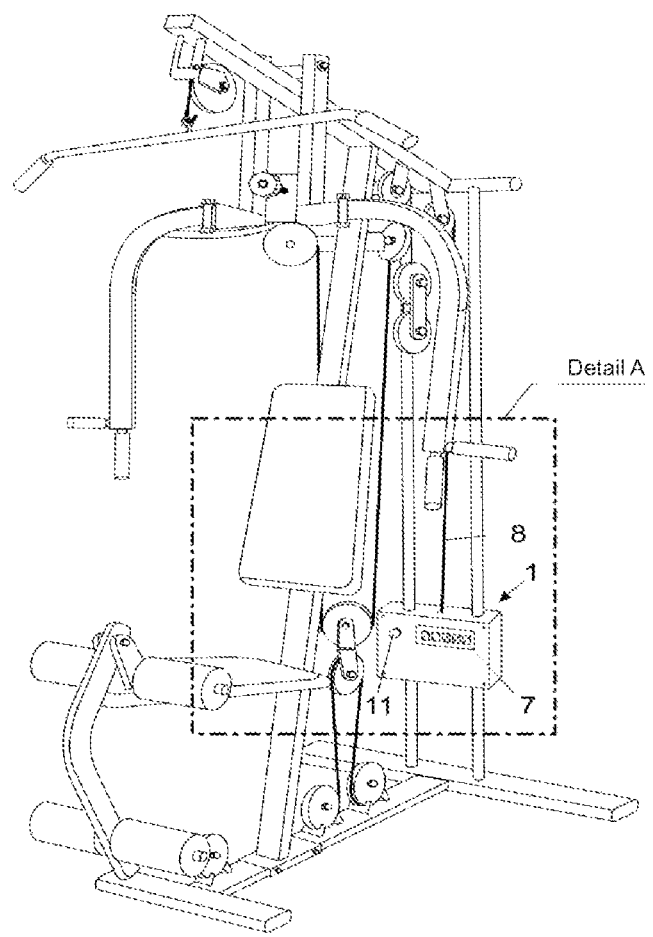
FIG. 3—detail A—represents the enlargement and the demonstration of the system inserted into already known exercise devices.

The system (1) described herein is relatively small, depending basically on the size of the pulley (3). This system (1) can be either coupled to already existing systems of weights—FIGS. 2 and 3, for example, professional or domestic bodybuilding stations, or inserted into developed equipment that is planned only for it, where there is a greater integration and design, for example, interaction with smartphones, tablets, use of a coded card (e.g., subway card), biometric recognition (facial or digital) and touch screens, etc.

Precisely because it is small and light, the system (1) described herein can be attached directly onto the wall—FIGS. 4 and 5—so that the cable (8) can be used freely, with an exit point either below or above. It can be seen that, due to the spring (10), the whole system is always stored in an organized manner. Therefore, it is concluded that the entire system (1) may be inside a housing—FIGS. 4 and 5—because all the parts can be mounted close to each other, including the speed selector (11) and the digital panel (7)—or only with the digital panel (7) positioned elsewhere. Also, in an embodiment of the invention, the digital panel (7) can be removed in order to reduce system costs, whereby the speed selector (11) can be placed in the housing itself, in a single unit.

Preferential examples of speed selectors (11) are the following selectors: digital or analog, those with a keyboard, potentiometer, buttons and speed controls actioned remotely that can be performed by a remote control, smartphones and similar devices.

Figure 4:
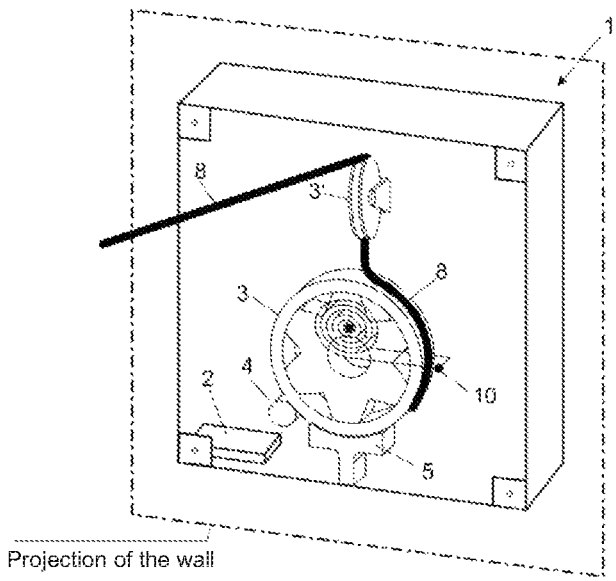
FIG. 4 represents a rear view of the projection of the system for the performance of exercises attached to the wall.
Figure 5:
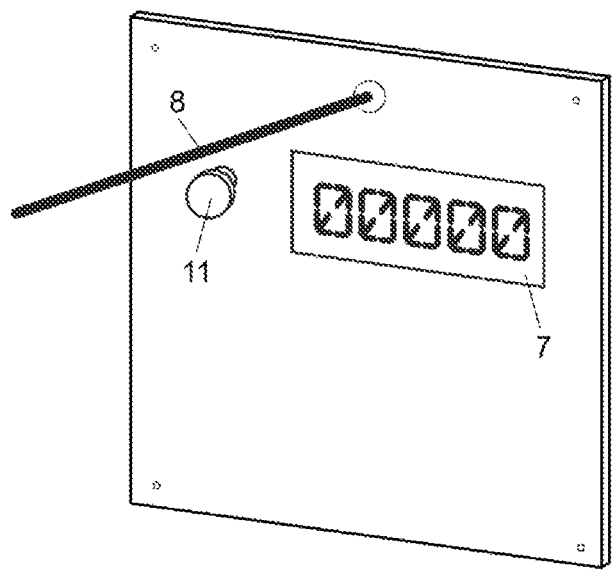
FIG. 5 represents the front view of the projection of the system for the performance of exercises attached to the wall.

Therefore, this housing can be fixed onto the wall or any other base, at the height that the user wants—FIGS. 4 and 5. For greater convenience, the housing may also be supplied with an extra pulley (3) at the exit point of the cable (8), in order to direct it horizontally. In this way, it is a system (1) that fits into one housing, making it a practical and useful system.

Finally, another example of an embodiment of the invention is the operation of the entire system (1) only as electric motors, in order to maintain the basic principle of the system based on the idea of speed and force. With this, the use of the brake (5) is not required or the sensor or the dynamometer (9). What is required in order to guarantee the safety of the system is only the use of the information panel (7) and the speed selector (11). If there is no force being employed, the system interprets that there is no exercise being practiced and interrupts the operation of the motor and returns everything back to the original position.

The system described by the present invention can also be assembled based on an electric motor (15), coupled or not to a gearbox (16), in order to provide a high torque. In this situation, specific software takes care of maintaining the central idea of the system, which is the constant speed of the movement, independent of the force employed by the user. The speed selector (11), the dynamometer (9) and the panel (7) would be maintained with all the information described previously. In this situation, there is the possibility of the performance of the eccentric movement, simply by reversing the rotation of the motor, in addition to the performance of the concentric movement, which is identical to the previously described mechanical system.

The present invention has been disclosed in this specification in terms of its preferred embodiment. However, other embodiments and variations are possible from the present description and can also be inserted into the scope of the invention disclosed herein.

The invention claimed is:

1. An exercise apparatus system that is comprised of a microprocessor, a pulley, a speed sensor, a brake, a support bar, a digital panel, a cable, a dynamometer, a spring, a speed selector and a program, wherein the microprocessor controls actuation of the brake of the pulley based on a speed that is pre-determined by a user and an instant speed measured by the sensor, and also receives information from the sensor, the dynamometer and the speed selector, whereby the speed, once regulated by the speed selector, is constantly measured by the sensor, which conveys the information to the microprocessor that controls the brake of the pulley, keeping a rotation speed of the pulley constant, as set previously by the speed selector of the pulley; and the dynamometer installed on the cable supplies information on force applied on the support bar to the microprocessor which is then displayed on the digital panel, wherein a steel cable is attached to the pulley and connected to the support bar, and wherein a minimum force must be applied to the bar in order to overcome resistance of the spring.

2. A system in accordance with claim 1, further comprising a second pulley.

3. A system in accordance with claim 1, wherein the brake is a disk, electromagnetic drum, or electro-hydraulic, and has a capacity for a force of up to 500 kg.

4. A system in accordance with claim 1, wherein the cable comprises a load sensor and that supplies information on the force applied, which is shown on the panel.

5. A system in accordance with claim 1, wherein the spring is helical or spiral and configured to bring the system back to its initial status.

6. A system in accordance with claim 1, wherein the speed selector is digital, analog, keyboard, potentiometer, button, touchscreen display or activated remotely.

7. A system for performing physical exercises at a constant speed of a movement, the system comprising a microprocessor, a pulley, a speed sensor, a brake, a support bar, a digital panel, a steel cable, a dynamometer, a spring, and a speed selector,
   wherein the steel cable is attached to the pulley and connected to the support bar, wherein the dynamometer is installed on the steel cable, and
   wherein the spring is attached to the pulley and, in order to overcome the resistance of the spring, a minimum force must be applied to the support bar,
   wherein based on an input of a user of the system, the speed selector is configured to receive an information of a desired speed for performing the physical exercise and to forward said desired speed information to the microprocessor, the dynamometer is configured to constantly measure the force that pulls the steel cable and to forward said force information to the microprocessor, the speed sensor is configured to constantly measure an instantaneous rotation speed of the pulley and to forward said instantaneous rotation speed information to the microprocessor,
   wherein a program is associated with the microprocessor, which program, based on the received desired speed information from the speed selector and on the received instantaneous rotation speed information of the pulley, is configured to control the brake of the pulley in order to maintain a constant rotation speed of the pulley, so that the speed of movement of the support bar is maintained constant independent of the force being applied to it by the user, either by releasing the pulley when it rotates below the programmed speed, or by pressing on the pulley when it rotates above the programmed speed, and wherein the microprocessor is further configured to forward the force information received from the dynamometer to the digital panel, which digital panel is configured to display the force being exerted by the user on the support bar.

8. The system in accordance with claim 7, wherein the system further comprises a second pulley.

9. The system in accordance with claim 7, wherein the brake is a disk, an electromagnetic drum or electrohydraulic and it has a capacity for a force of up to 500 kg.

10. The system in accordance with claim 7, wherein the spring is helical or spiral and is configured to bring the system back to its initial status.

11. The system in accordance with claim 7, wherein the speed selector is digital, analog, a keyboard, a potentiometer, buttons, a touchscreen display or a remotely activated device.

* * * * *